US00PP36407P2

(12) United States Plant Patent
Garner

(10) Patent No.: US PP36,407 P2
(45) Date of Patent: Jan. 21, 2025

(54) ***PHILODENDRON* PLANT NAMED 'Tropic Blush'**

(50) Latin Name: ***Philodendron* hybrid**
Varietal Denomination: Tropic Blush

(71) Applicant: Lawrence 'Lariann' Garner, Clewiston, FL (US)

(72) Inventor: Lawrence 'Lariann' Garner, Clewiston, FL (US)

( * ) Notice: Subject to any disclaimer, the term of this patent is extended or adjusted under 35 U.S.C. 154(b) by 0 days.

(21) Appl. No.: 18/766,124

(22) Filed: Jul. 8, 2024

(51) Int. Cl.
*A01H 5/12* (2018.01)
*A01H 6/10* (2018.01)

(52) U.S. Cl.
USPC ..... Plt./381

(58) Field of Classification Search
USPC ..... Plt./373, 381
See application file for complete search history.

(56) References Cited

U.S. PATENT DOCUMENTS

PP34,347 P2 * 6/2022 Garner ..... Plt./381

* cited by examiner

*Primary Examiner* — Karen M Redden
(74) *Attorney, Agent, or Firm* — James R. Holm; Plant Novelty Rights, LLC

(57) ABSTRACT

A new and distinct *Philodendron* plant named 'Tropic Blush' particularly distinguished by uniquely visible and pronounced lateral leaf venation, thus more numerous interveinal leaf segmentation, foliage that turns a dark, shiny green as foliage matures, durability and relative freedom from pests, is disclosed.

3 Drawing Sheets

Figure 1:
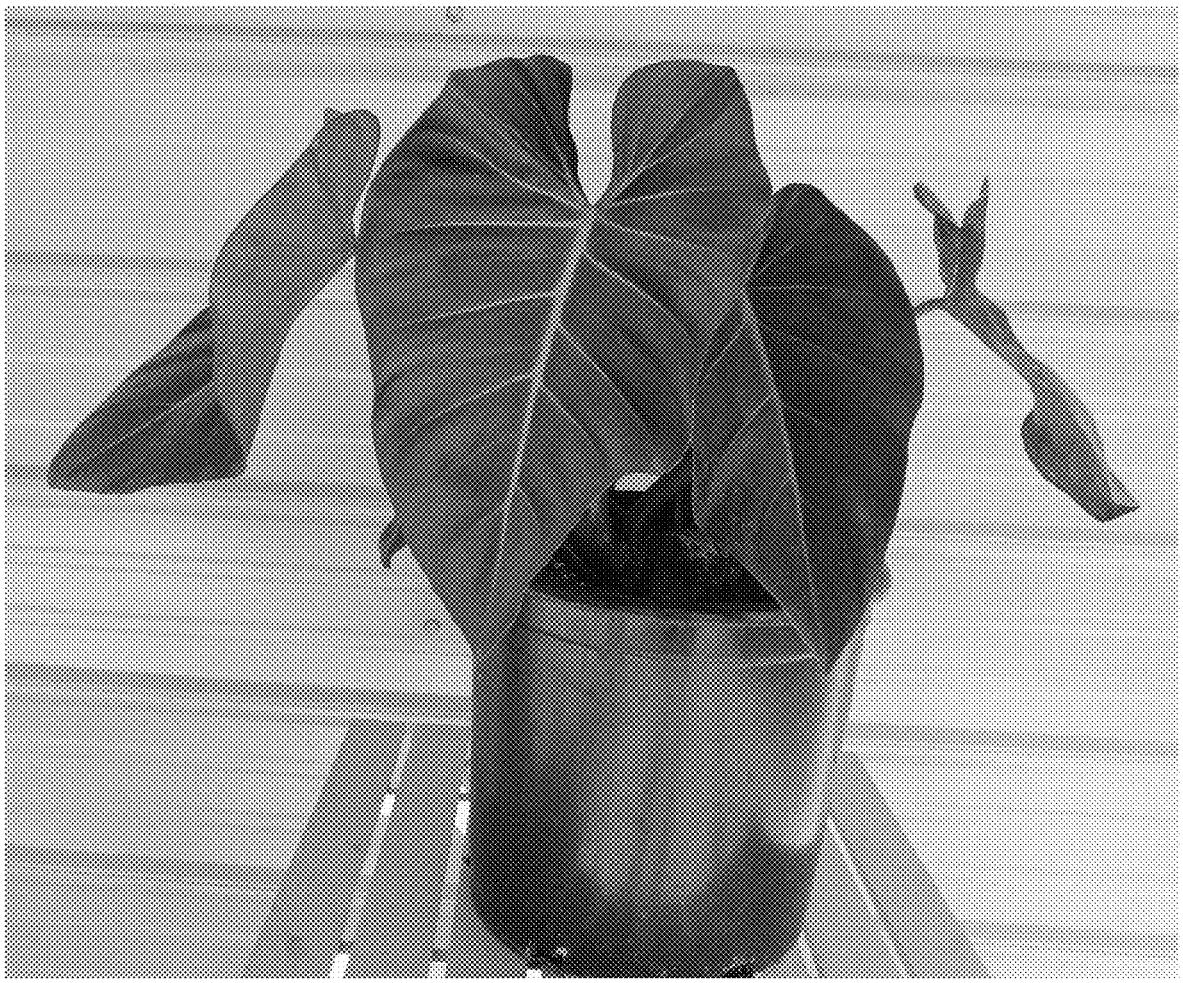

Genus and species: *Philodendron* hybrid.
Cultivar denomination: 'Tropic Blush'.

BACKGROUND OF THE NEW PLANT

The present invention comprises a new and distinct interspecific hybrid plant of *Philodendron*, hereinafter referred to by its cultivar name 'Tropic Blush'.

The new cultivar was derived from a controlled breeding program conducted by the inventor at a nursery in Florida City, Florida. The overall purpose of the breeding program is to make new selections of *Philodendron* plants with unique foliage that are cold resistant and durable with a good growth rate in Florida. 'Tropic Blush' is the product of a controlled cross made by the inventor in August 2016 between an unnamed "McColley" hybrid *Philodendron* as the female parent (unpatented) and an unnamed *Philodendron gloriosum* as the male parent (unpatented). 'Tropic Blush' was selected by the inventor as a single unique plant in Florida City, Florida from amongst progeny plants derived from said cross. 'Tropic Blush' is a sibling of *Philodendron* plant named 'Summer Glory' (U.S. Plant Pat. No. 34,347).

The new cultivar was selected based on its more visible and pronounced lateral leaf venation, as compared to 'Summer Glory', and for its durability and relative freedom from pests as compared to other commercially available *Philodendron* cultivars. 'Tropic Blush' was first reproduced asexually by vegetative cuttings in Florida City, Florida in May 2022. Asexual propagation by vegetative cuttings of the new cultivar has shown that the unique features of the new cultivar are stable and reproduced true-to-type.

Plant Breeder's Rights for this new cultivar have not been applied for. 'Tropic Blush' has not been made publicly available or sold anywhere in the world prior to the effective filing date of this application.

SUMMARY OF THE INVENTION

The new *Philodendron* cultivar has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Philodendron* cultivar. The combination of these characteristics distinguishes 'Tropic Blush' as a new and distinct cultivar of *Philodendron:*

1. Uniquely visible and pronounced lateral leaf venation;
2. More numerous interveinal leaf segmentation;
3. Foliage that turns a dark, shiny green as foliage matures;
4. Durability; and
5. Relative freedom from pests.

DESCRIPTION OF THE PHOTOGRAPHS

This new *Philodendron* cultivar is illustrated by the accompanying colored photographs which show the overall appearance and distinct characteristics of the plant. The colors shown are as true as can be reasonably obtained by conventional photographic procedures. The photographs are of a 2.5-year-old plant grown in a 2-gallon container under 60 to 90 percent shade in greenhouse in Florida City, Florida. Colors in the photographs may differ slightly from the color values cited in the botanical description which accurately describes the colors of the new cultivar.

FIG. 1. shows a side view of the overall plant form and foliage of 'Tropic Blush'.

Figure 2:
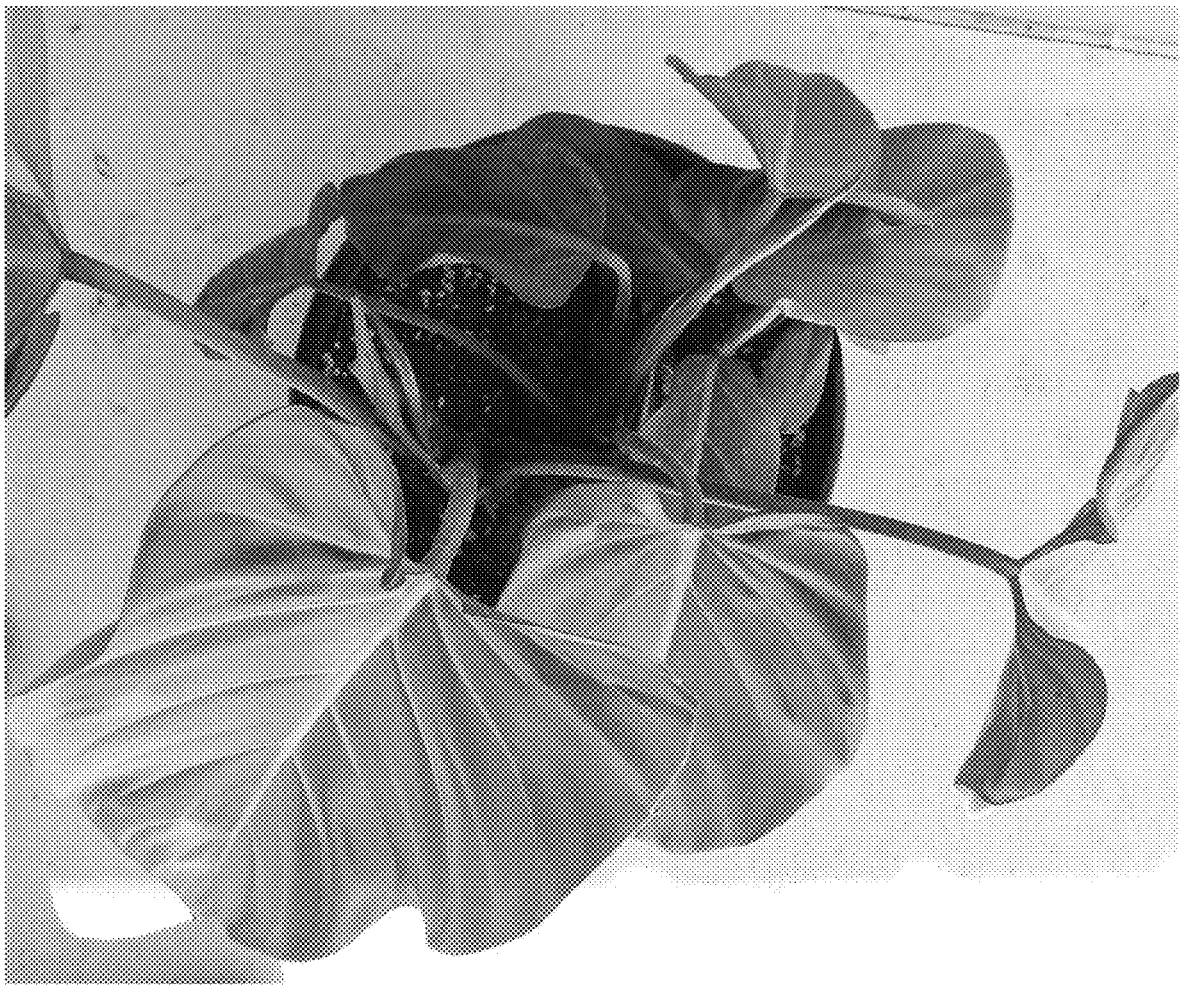

FIG. 2. shows a top view of the inner crown of 'Tropic Blush'.

Figure 3:
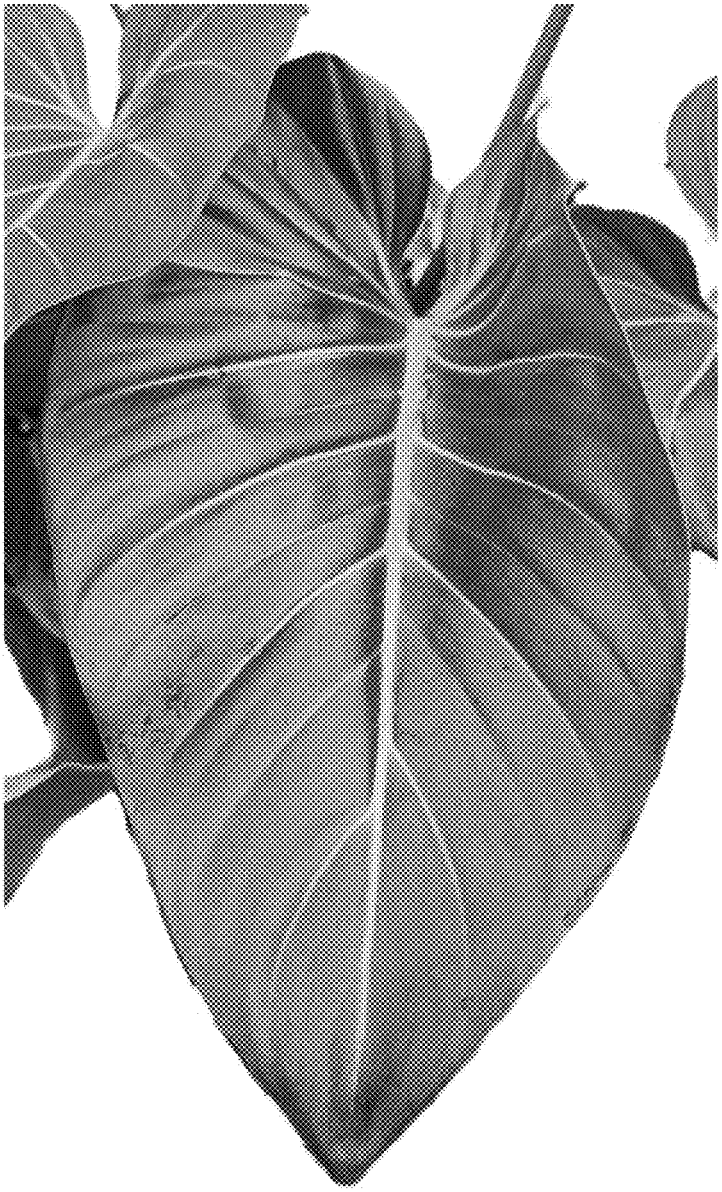

FIG. 3. shows a closeup of a mature leaf of 'Tropic Blush'.

DESCRIPTION OF THE NEW CULTIVAR

In the following description, color references are made to The Royal Horticultural Society Colour Chart, Sixth Edition, except where general color terms of ordinary dictionary significance are used.

The following observations and measurements describe plants grown under 60 to 90 percent shade in greenhouse in Florida City, Florida. Detailed descriptions were taken in April and May 2024 from a 2.5-year-old plant grown in a 2-gallon container. Measurements and numerical values represent averages of typical plant types.

DETAILED BOTANICAL DESCRIPTION

Classification:

*Family*.—Araceae.

*Botanical*.—*Philodendron* hybrid.

*Common*.—*Philodendron*.

*Denomination*.—'Tropic Blush'.

General description:

*Plant type*.—Tropical perennial.

*Growth habit*.—Upright and arching.

*Height from soil level to top of foliar plane*.—54.0 cm.

*Plant spread*.—92.0 cm.

*Number of basal shoots per plant*.—4.

*Stems*.—Approximately 3.0 cm in diameter.

*Growth rate*.—Moderate.

*Propagation type*.—Vegetative cuttings.

*Time to initiate rooting*.—2 weeks.

*Time to produce a rooted cutting*.—3 weeks.

*Roots*.—Fleshy and fibrous, colored brownish orange, 171B.

Foliage description:

*Quantity of leaves per plant*.—Approximately 6 to 8.

*Arrangement*.—Alternate.

*Attachment*.—Petiolate.

*Division*.—Simple.

*Lamina*.—Shape: Broadly cordate. Length: 36.0 cm. Width: 25.0 cm at the widest point. Orientation: Held horizontal to slightly downward. Apex: Aristate. Base: Deeply lobed, lobes about 10.0 cm in depth and 9.0 cm in width. Aspect: Moderately concave. Margins: Entire, slightly to moderately undulate. Texture and luster, adaxial surface: Smooth, glabrous and glossy. Texture and luster, abaxial surface: Smooth, glabrous and moderately glossy. Color: Juvenile foliage, adaxial surface: Reddish bronze, 173A. Juvenile foliage, abaxial surface: Grayish red, 176B, edges are dark red, 183A. Mature foliage, adaxial surface: Overall dark green, NN137A, with faint streaking of yellow-green, NN144A. Mature foliage, abaxial surface: Reddish brown, 177A. Venation: Pattern: Pinnate. Color, adaxial surface: Purplish pink, 186C to 186D on younger foliage, venation color fades with age. Color, abaxial surface: Green, 137B to 137C.

*Petiole*.—Strength: Moderately strong. Shape in cross-section: Very widely ovate. Length: 30.0 cm. Width: 2.0 cm at point of attachment to main stem, narrowing to 1.0 cm at point of attachment to the base of the lamina. Orientation: Approximately 45 to 60 degrees from the central vertical axis. Texture and luster, adaxial surface: Slightly raised, broken linear striations are present, otherwise glabrous, and slightly glossy. Color: Mostly green, 137B, with a deltoid shaped region at the base colored dark red, 187A to 187B; linear striations are colored gray, 195A, with a slight tint of purplish pink, 186D.

*Cataphyll*.—Description: Double keeled. Shape: Lanceolate. Length: 22.0 cm. Width: 3.0 cm at the base, narrowing towards the apex, 0.5 cm. Color: Dark red, 59A to 59B, turning lighter red towards the base.

Inflorescence: None observed.

Cold tolerance: Can tolerate down to or near freezing temperatures (30 to 34 degrees F.).

Disease and pest tolerance: Good.

Fruit and seed set: None observed.

Drought tolerance: Good.

COMPARISON WITH PARENTAL CULTIVARS

'Tropic Blush' differs from the female parent *Philodendron* plant in that 'Tropic Blush' has unique and attractive leaf and plant coloration, and the growth habit is semi-recumbent to upright. 'Tropic Blush' differs from the male parent *Philodendron* plant in that 'Tropic Blush' has a greater number of leaves on maturity and does not creep along the ground as the male parent does. Stem internodes of 'Tropic Blush' are much shorter compared to the male parent.

COMPARISON WITH COMMERCIAL CULTIVARS

When compared to the sibling and commercial *Philodendron* plant named 'Summer Glory', 'Tropic Blush' has much more visible and pronounced lateral leaf venation. The interveinal leaf segmentation of 'Tropic Blush' is thus more numerous in appearance compared to leaves of 'Summer Glory'. Additionally, leaves of 'Tropic Blush' are broadly cordate in shape, whereas leaves of 'Summer Glory' are cordate to sagittate in shape.

I claim:

1. A new and distinct cultivar of *Philodendron* plant named 'Tropic Blush', substantially as illustrated and described herein.

* * * * *